United States Patent
Maschke

(10) Patent No.: US 8,452,397 B2
(45) Date of Patent: May 28, 2013

(54) IMPLANTABLE PACEMAKER

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 1727 days.

(21) Appl. No.: 11/731,895

(22) Filed: Mar. 30, 2007

(65) Prior Publication Data

US 2007/0233200 A1 Oct. 4, 2007

(30) Foreign Application Priority Data

Mar. 31, 2006 (DE) .......................... 10 2006 015 013

(51) Int. Cl.
*A61N 1/00* (2006.01)

(52) U.S. Cl.
USPC ............................................................ 607/9

(58) Field of Classification Search
USPC .................................... 607/9, 27, 36, 63
See application file for complete search history.

(56) References Cited

U.S. PATENT DOCUMENTS

| | | | |
|---|---|---|---|
| 4,038,990 A * | 8/1977 | Thompson ........................ | 607/9 |
| 4,162,679 A * | 7/1979 | Reenstierna ................... | 607/122 |
| 4,258,724 A * | 3/1981 | Balat et al. ..................... | 607/128 |
| 4,280,512 A * | 7/1981 | Karr et al. ..................... | 607/128 |
| 4,320,726 A * | 3/1982 | Etoh et al. ..................... | 123/672 |
| 4,320,763 A * | 3/1982 | Money ............................. | 607/9 |
| 4,726,383 A * | 2/1988 | Cook et al. ...................... | 607/21 |
| 4,809,713 A * | 3/1989 | Grayzel ......................... | 607/116 |
| 5,109,112 A | 4/1992 | Siekierka et al. | |
| 5,193,546 A * | 3/1993 | Shaknovich ................... | 600/463 |
| 5,217,010 A | 6/1993 | Tsitlik et al. | |
| 5,540,959 A | 7/1996 | Wang | |
| 5,827,997 A | 10/1998 | Chung et al. | |
| 6,241,671 B1 | 6/2001 | Ritter et al. | |
| 6,330,467 B1 | 12/2001 | Creighton, IV et al. | |
| 6,506,972 B1 * | 1/2003 | Wang .............................. | 174/36 |
| 6,673,999 B1 | 1/2004 | Wang et al. | |
| 6,713,671 B1 | 3/2004 | Wang et al. | |
| 6,772,001 B2 * | 8/2004 | Maschke ........................ | 600/423 |
| 6,937,906 B2 * | 8/2005 | Terry et al. ...................... | 607/63 |
| 7,509,174 B2 * | 3/2009 | Imran et al. ................... | 607/133 |
| 2002/0019644 A1 | 2/2002 | Hastings et al. | |
| 2002/0042645 A1 | 4/2002 | Shannon | |
| 2002/0123505 A1 | 9/2002 | Mollison et al. | |
| 2002/0133204 A1 * | 9/2002 | Hrdlicka et al. ................ | 607/11 |
| 2003/0083726 A1 * | 5/2003 | Zeijlemaker et al. ......... | 607/122 |
| 2003/0100887 A1 | 5/2003 | Scott et al. | |
| 2003/0140931 A1 * | 7/2003 | Zeijlemaker et al. ......... | 128/899 |
| 2003/0152609 A1 | 8/2003 | Fischell et al. | |
| 2004/0158142 A1 * | 8/2004 | Hall et al. ..................... | 600/374 |
| 2005/0070985 A1 * | 3/2005 | Knapp et al. ................... | 607/122 |

(Continued)

FOREIGN PATENT DOCUMENTS

DE 28 43 096 A1 4/1980
DE 33 00 050 C2 7/1984

(Continued)

*Primary Examiner* — Eric D. Bertram
*Assistant Examiner* — Roland Dinga

(57) ABSTRACT

A pacemaker comprises an implantable pacemaker housing and a pacemaker electrode which is provided for the transmission of stimulation pulses. A switching element, in particular a reversibly actuatable switching element, is provided for interrupting, reducing or limiting a current flowing through the pacemaker electrode, said current being inducible by an external magnetic field. Parts of the pacemaker are coated with a material, in particular a nanostructured material, which counteracts magnetic effects.

16 Claims, 7 Drawing Sheets

U.S. PATENT DOCUMENTS

| | | | |
|---|---|---|---|
| 2006/0025834 A1* | 2/2006 | Von Arx et al. | 607/60 |
| 2006/0190068 A1* | 8/2006 | Maschke | 607/126 |
| 2007/0067004 A1* | 3/2007 | Boveja et al. | 607/45 |
| 2007/0203547 A1* | 8/2007 | Costello et al. | 607/59 |
| 2009/0138058 A1* | 5/2009 | Cooke et al. | 607/5 |

FOREIGN PATENT DOCUMENTS

| | | |
|---|---|---|
| DE | 198 27 460 A1 | 12/1998 |
| DE | 102 03 371 A1 | 8/2003 |
| DE | 102 03 372 A1 | 9/2003 |
| DE | 102 55 957 A1 | 8/2004 |
| DE | 10 2004 062 399 A1 | 7/2006 |
| EP | 0 356 399 A2 | 2/1990 |
| EP | 0 534 401 B1 | 3/1993 |
| EP | 0 701 802 B1 | 3/1996 |
| EP | 0 882 469 B1 | 12/1998 |

* cited by examiner

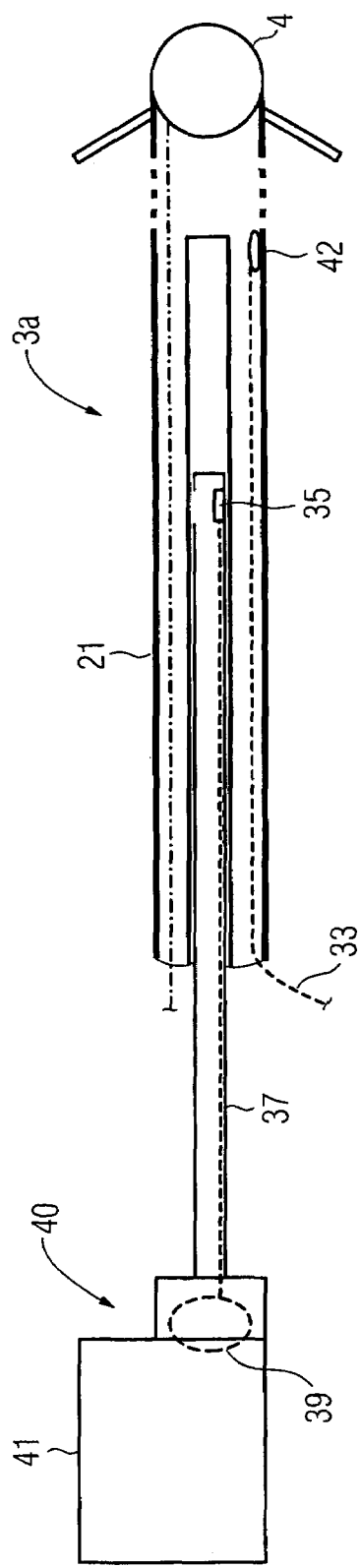
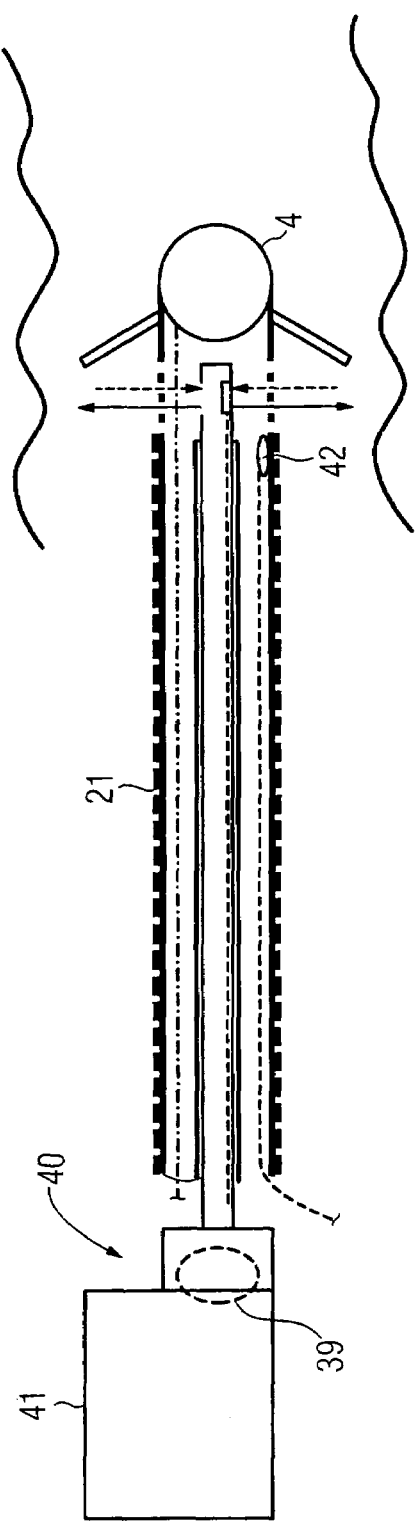

IMPLANTABLE PACEMAKER

CROSS REFERENCE TO RELATED APPLICATIONS

This application claims priority of German application No. 10 2006 015 013.9 filed Mar. 31, 2006, which is incorporated by reference herein in its entirety.

FIELD OF THE INVENTION

The invention relates to a pacemaker comprising an implantable pacemaker housing and a pacemaker electrode which is provided for the transmission of stimulation pulses to the heart.

BACKGROUND OF THE INVENTION

A pacemaker of this type is known for example from EP 0 882 469 B1. A pacemaker electrode is known for example from DE 33 00 050 C2.

Implantable pacemakers are operated either with unipolar pacemaker electrodes or with bipolar pacemaker electrodes. In the case of a unipolar electrode, the electrode tip of the pacemaker electrode operates as a cathode and the pacemaker housing as an anode. The bipolar systems match the unipolar systems insofar as they also operate with a cathodic electrode tip. In contrast to the unipolar systems, however, in bipolar pacemaker electrodes an anode is additionally arranged in the distal area of the electrode. Pacemaker electrodes which serve to transmit stimulation pulses from a pulse generator arranged in the pacemaker housing to the heart, in particular to the atrium and/or to the ventricle, can be advanced with the aid of an introducer through a vein to the heart, it being possible for this procedure to be monitored under X-ray fluoroscopy.

Both in the case of unipolar pacemaker electrodes and in the case of bipolar pacemaker electrodes complications can arise if the patient wearing the pacemaker is exposed to a strong magnetic field. Strong magnetic fields of up to 7 Tesla occur in particular in magnetic resonance devices. If the magnetic field is changed and/or the pacemaker electrode is moved in the magnetic field, then currents are induced which may lead to intense heating of the pacemaker electrode and to irreversible tissue damage. For this reason, patients with a pacemaker according to the prior art cannot be examined in magnetic resonance devices.

SUMMARY OF THE INVENTION

The object of the invention is to reduce restrictions that exist for patients carrying a pacemaker in medical examinations.

This object is achieved by an implantable pacemaker according to the claims. This pacemaker has an implantable pacemaker housing and at least one pacemaker electrode which is provided for the transmission of stimulation pulses to the heart. In order at least to weaken currents induced by a magnetic field in the pacemaker electrode, at least one switching element, in particular a reversibly actuatable switching element, i.e. enabling multiple switching processes, is provided which can interrupt or limit the current flowing in the pacemaker electrode.

The invention can also be applied to other implantable medical products which are provided for delivering electrical pulses, in particular to ICDs (implantable cardioverters/defibrillators) and/or neurostimulators.

Preferably, a semiconductor switching element, for example in transistor or thyristor technology, in particular in the form of an integrated circuit, is used as a switching element. Particularly advantageous is the use of a switching element which comprises a Zener diode or is formed by a Zener diode. The Zener diode becomes conductive when a particular voltage is exceeded and, if suitably arranged, can thus at least largely suppress relaying of a current induced by a magnetic field to the tip of the pacemaker electrode. An adequate blocking effect can be achieved in normal operation of the pacemaker by two Zener diodes connected back to back to form a limiter.

The switching element can be fashioned as a simple switch, which is generally understood to be a component by means of which an electric circuit can be interrupted or closed. In a broader sense, however, a switch is in the present case also deemed to be a component which does not fully interrupt an electric circuit but serves only to limit or reduce a current. The terms "switch" and "switching element" are used synonymously hereinbelow, unless explicitly mentioned otherwise.

A switch is understood to be both a component for the multiple opening and closing of an electric circuit and a component which enables merely a one-off opening of a line, in particular a fuse. In a particularly simple embodiment, the pacemaker electrode is monitored by means of a melting fuse, which, in the event of a current being generated by an external magnetic field, melts if the temperature increases as a result. In this case, the patient will need a new electrode cable. Replacement of the pacemaker electrode, however, is associated with a substantially lower strain on the patient than possible effects of a strong magnetic field.

A switchability of the reversible switching element via telemetry is particularly advantageous. The at least one switching element can thus be opened from outside the patient before the patient is exposed to a strong magnetic field. While no further stimulation pulses can be transmitted to the heart after the switching element has been opened, this can generally be allowed for since, while the examinations on the basis of which the pacemaker is deactivated are being carried out, the patient will be under supervision by a doctor. The cardiac activity can be monitored, for example, via ECG. Where necessary, the cardiac activity can also be selectively supported by drugs during the examination.

In a variant that can be combined with the embodiment illustrated above, switching processes of the reversible switching element take place automatically depending on the strength of an existing magnetic field. In this case, the magnetic field can, for example, be measured via the current induced in the pacemaker electrode. The triggering of the switching element is preferably rendered detectable by means of telemetry. The closing of the switching element, i.e. renewed activation of the pacemaker after a preceding automatic shutdown can, in the event of a magnetic field falling below an admissible threshold value, be carried out either automatically or after clearance by specialist medical personnel, preferably triggerable via telemetry. A switching element that automatically opens and re-closes can also operate temperature-dependently, for example as a bimetal switching element or as a semiconductor circuit with temperature-dependent properties.

The pacemaker preferably has only metal components that are not ferromagnetic, and is therefore specifically designed for strong magnetic fields. Unless an external magnetic field exceeds an admissible threshold value, the stimulation frequency of the pacemaker is in a preferred embodiment not dependent on external magnetic fields. In contrast with this, some pacemakers according to the prior art can in a selective manner be affected by external magnetic fields, in particular set to a fixed stimulation frequency. In the pacemaker according to the invention, such dependencies of the mode of operation of the pacemaker on a magnetic signal can, provided the admissible threshold value for the magnetic field is not exceeded when the pacemaker is active, preferably be disabled or generally not provided.

According to an advantageous development, the pacemaker electrode has a magnet, in particular an electromagnet, that enables a selective navigation, controlled by an external magnetic field, of the pacemaker electrode. A navigation system of this type for medical products such as endoscopes or catheters is principally known, for example, from DE 102 03 371 A1, DE 102 03 372 A1, and from US 2002/0019644 A1 and U.S. Pat. No. 6,330,467 B1.

According to a further variant that can advantageously be combined with the embodiment described above, the pacemaker electrode has a measurement element for an ultrasound examination and/or a measurement element for optical coherence tomography (OCT). Here, a duct and a conductor leading to the electrode head run in the electrode cable which has an insulating sleeve. An ultrasound catheter and/or a measuring device for optical coherence tomography can be inserted into the duct of the electrode cable, the ultrasound catheter or the measuring device having a thread-like guide element and a measurement element for an ultrasound measurement or an OCT measurement that functions with visible and/or non-visible light attached to its distal end. The guide element preferably serves both to advance the at least one measurement element in the electrode cable as well as to transmit electrical signals.

An ultrasound measurement element is understood to be a measurement element which comprises both an ultrasound transmitter and an ultrasound receiver. The combination of the pacemaker electrode with the ultrasound measurement element enables an imaging diagnosis with good resolution in the heart. This diagnosis is particularly advantageous if X-ray fluoroscopy is performed simultaneously. The ultrasound catheter is not permanently linked to the other parts of the pacemaker electrode but is only introduced into the duct of the electrode cable if necessary. Similar also applies to the OCT measuring device.

The OCT measurement method is principally known for example from DE 102 55 957 A1 which relates to a medical examination and/or treatment system. In comparison to measurement with ultrasound, also referred to as IVUS (intravascular ultrasound system) measurement, OCT measurement is distinguished by a substantially higher resolution, but with a lower depth of penetration. Consequently, IVUS measurement and ultrasound measurement can complement one another. An IVUS measurement system is principally known for example from DE 198 27 460 A1 as well as from U.S. Pat. No. 5,193,546 A.

The duct of the electrode cable is preferably closed to such an extent that the ultrasound catheter and/or OCT catheter cannot come into contact with the patient's blood or body tissue. Thus the catheter provided for the imaging measurement can readily be used more than once, even with different patients. The region of the electrode cable bordering the electrode head is preferably designed such that an IVUS and/or OCT measurement is possible that is to a large extent uninfluenced by the material of the pacemaker electrode. For this purpose, an axial distance between the distal end of the duct and the electrode head is advantageous, it being possible for the measurement catheter, in particular the ultrasound and/or OCT measurement element thereof, to be advanced beyond the duct towards the electrode head. Preferably, at least one window which is transparent for the waves used for measuring, namely ultrasound waves or electromagnetic waves, in particular in the infrared range, for example a window ring, is arranged in the area of the insulating sleeve of the electrode cable bordering the electrode head.

According to a preferred development, a fluid duct suitable for conveying a contrast means towards the electrode head, and comprising an outlet opening in front of the electrode head, is provided, independent of whether the electrode cable has a duct for an IVUS and/or OCT catheter. Where a duct for an ultrasound catheter or an OCT catheter is present, provision can also be made for guiding the contrast means through the same duct which is also suitable for introducing the measurement catheter. The use of a contrast means substantially broadens the diagnostic possibilities, in particular in combination with an ultrasound examination. In the case of an OCT measurement, in particular a cooking salt solution can be guided through the fluid duct, which significantly improves the optical coherence tomography results that can be achieved.

The outlet opening of the fluid duct preferably comprises a sealing device which, in the manner of a non-return valve, prevents body fluids from flowing into the electrode cable. Independenttof the total number of ducts in the electrode cable, provision is preferably made, where an IVUS or OCT measurement is intended, for an exit opening for the measurement catheter in the region of the electrode head. This allows the measurement element to be advanced past the electrode head or, provided that the exit opening is located in the electrode head, just beyond the electrode head.

Similarly to the outlet opening for the contrast means, the exit opening for the measurement element can optionally also be preferably sealed by means of a valve. This valve can, for example, be held in a closed state by means of spring force and opened by means of magnetic force. In this case, a magnet, in particular an electromagnet, is preferably arranged in the valve or mechanically coupled thereto.

A particularly reliable sealing of the exit opening for the measurement element can be realized by means of a membrane, which seals the exit opening and is elastic such that the measurement catheter can be displaced beyond the electrode head when an exit opening remains sealed. In this embodiment, the exit opening is preferably arranged at the distal end of the. The measurement catheter in this embodiment is preferably rotatably arranged in a protective tube, which—without rotating—can be displaced in the electrode cable and therebeyond.

In the aforementioned embodiments in particular, the pacemaker can, together with an evaluation unit, form a diagnostic and treatment device. This diagnostic and treatment device is preferably configured in a programming manner such that the measurement element which can be used for an imaging diagnostic method interacts with the evaluation unit such that influences of the conductor of the electrode cable on the OCT, IVUS or other imaging measurement are computationally at least partially eliminated. The evaluation unit allows in a preferred embodiment different pacemaker electrodes to be taken into account computationally. For this purpose, the evaluation unit is coupled to a data acquisition device which is provided to record data, in particular geometric data, of the pacemaker electrode. This allows different conductor geometries to be practically removed from the images obtained by means of the examination, in particular OCT or IVUS examination. In the same way as the geometry of the conductor, other geometric features of the pacemaker electrode can also be taken into account computationally in this way.

In this embodiment, the pacemaker preferably also has, in interaction with additional parts of the diagnostic and treatment device, telemetry facilities. In this case, a telemetry module is arranged in the pacemaker housing, to which the electrode cable is connected. Where the pacemaker comprises electrode measurement elements, these are also connected to the telemetry module. This also applies to cases of sensing, i.e. of reading out signals from the heart via the pacemaker electrode.

In all embodiments of pacemakers there is in principle the possibility that the stimulation threshold will change over the course of time as a result of tissue fibrosis in the region of the electrode tip. Such a change in the stimulation threshold leads in extreme cases to the pacemaker no longer fulfilling the function for which it was intended. The pacemaker electrode achieves long-term usability with particularly low changes in the stimulation threshold over time according to a further development, whereby the electrode tip of the pacemaker electrode is fashioned for releasing an active substance. The electrode tip preferably has a number of recesses in which an active substance is held and/or on which an active substance is deposited. The quantity of active substance and the release rate from the electrode tip are preferably measured such that the active substance is released from the implanted electrode tip continuously over a period of at least 1000 hours, preferably over a period of at least 2 months, for example about 3 months.

Tissue fibrosis can be prevented or at least curtailed by means of the long-lasting release of the active substance, so that the stimulation threshold of the pacemaker is not increased significantly. After the cited time periods of significantly more than one month, the immune system of the patient has typically become adjusted to the electrode tip to such an extent that no further tissue fibrosis occurs and hence the stimulation threshold of the pacemaker remains at least approximately constant.

The drug released from the electrode tip preferably contains at least one of the following active substances:
sirolimus, known for example from US 2003/0100887 A1 and US 2002/0042645 A1,
paclitaxel, known for example from US 2003/0100887 A1 and US 2002/0042645 A1,
everolimus, known for example from US 2003/152609 A1,
fibrin, known for example from EP 0 701 802 B1,
rapamycin, known for example from US 2002/0123505 A1,
tacrolimus, known for example from EP 0 356 399 and U.S. Pat. No. 5,109,112, The first four active substances cited (sirolimus, paclitaxel, everolimus and fibrin) are also used for vascular supports called stents, which are suitable for releasing active substances. Sirolimus, also known as Rapamune, is an immunosuppressant that was developed to reduce organ rejection in the patient. Paclitaxel is classified as a natural product with an anti-tumor action and belongs to the group of antineoplastic agents. Everolimus is related to sirolimus and is also used to counter transplant rejection. Both substances are rapamycin analogs. The active substance tacrolimus is also known as FK 506.

The active substance fibrin, a naturally occurring polymer, that is produced during blood clotting from fibriogen under the action of thrombin, and is also used for example in fibrin glues in surgery, has the additional advantage that it can also increase the adhesion of the electrode tip to the myocardium.

The release rate of the active substance can be influenced, for example, by bioabsorbable materials, in particular polymers, or by biostable materials. In principle, measures which are described in connection with stents eluting an active substance (see above list of active substances and associated printed matter) are suitable here for influencing the activation and diffusion of the active substance. With regard to a barrier layer comprising an ion-exchange material that can be used for selective control of the release rate, the reader is referred to European patent EP 0 534 401 B1.

All the active substances cited can also be used in combinations. The drug eluted from the electrode tip can also comprise the following substances alone or in combination: actinomycin-d, methotrexate, doxorubicin, cyclophosphamide, 5-fluorouracil, 6-mercaptopurine, 6-thioguanine, cytoxan, cytarabinoside, cisplatin, chlorambucil, busulfan.

These active substances can be used in particular in order to prevent or suppress unwanted cell growth. All the substances cited can also be combined with other pharmacological substances, in particular anti-inflammatory agents such as Aspirin or Ibuprofen. In general, a drug comprising pharmacological, chemical, biological and/or genetic active substances can be released from the electrode tip. The active substances can, as described in even greater detail below, form a thin layer on the electrode tip or be fed continuously to the surface of the electrode tip from a reservoir located in the pacemaker electrode.

The electrode tip has an electrically conductive material, also referred to as the base material, which preferably contains platinum, carbon, titanium or combinations of these elements. The elements cited are particularly suitable for implantable medical products because of their physiological properties.

A ceramic material, aluminum dioxide, polyurethane or a polymer, is preferably provided as a coating material, with which the active substance comes into contact. In the latter case, coatings of meta-acrylate polymers are preferably used. The choice of coating material and the type of bond between the active substance and this material are jointly responsible for the release rate of the active substance from the electrode tip.

The electrical contact resistance of the electrode tip tends to be increased initially by the active substance. In order to reduce this effect, the active substance is preferably mixed with an electrolyte that reduces the electrical resistance. In the course of the service life of the pacemaker, the electrical contact resistance and hence the stimulation threshold is always substantially lower than in a pacemaker without drug release, which has led to tissue fibrosis.

According to a preferred development, the electrode tip has different active substances at different positions, preferably at intervals from one another. Equally, a mixture of active substances can also be applied to or fed to the electrode tip, it being possible for the mixture to be such that the individual active substances are released mainly in different time periods.

The active substance or combination of active substances is preferably introduced into the electrode tip in such a way that the release depends on the temperature, for example occurs solely in the temperature range from 35° C. to 42° C. The temperature-dependant active-substance release can be realized in particular by a recess in the electrode tip, in which the active substance is located, being sealed with a material that can degrade as a function of the temperature, for example passes into the liquid phase within the temperature interval cited. Where different active substances are located at the electrode tip, these are preferably introduced into the electrode tip in such a way that they are released with a different distribution over time. In this way, the drug release can be constantly adjusted within the overall release period of more than one month to the respective medical requirements. According to a further development, the drug release takes place over a period of at least 10 years, for example about 15 years. This period corresponds approximately to the service life of the pacemaker electrode. Even where a drug is released from the pacemaker electrode over such a long period, the first months after the implantation are the most significant.

Recesses in the electrode tip which are provided for holding the active substance or active substances can have a variety of different shapes, even within one and the same electrode tip. According to a particularly simple embodiment, the recesses are fashioned as sealed wells on the surface of the electrode tip. Here, the wells can be arranged in a geometrically defined manner on the surface of the electrode tip or distributed irregularly to form a rough surface overall. In the latter case, the roughness of the surface of the electrode tip has the purpose of providing better adhesion of the active substance, it being possible for the entire surface, which is at least very slightly roughened, to be covered with a thin active-substance layer. The rough surface of the electrode tip can be produced, for example, by means of etching techniques, even on the nanotechnology scale.

In the case of individual defined wells on the surface of the electrode tip, the active substance is preferably located exclusively in the wells. This approximately punctiform distribution of small volumes of active substance can be achieved by immersing the electrode tip initially in an immersion bath containing the active substance and thereby wetting it totally with active substance. After the active substance has dried on the surface of the electrode, it is abraded so that the active substance located outside the wells is removed and the underlying conductive surface of the electrode tip is re-exposed. The surface regions of the electrode tip outside the wells preferably occupy a larger area overall than the wells. In this way, the electrode tip retains a low contact resistance, which, as mentioned above, can be further reduced by adding an electrolyte to the active substance. The thickness of the active-substance layer applied to the electrode tip can easily be influenced by the number of coating and subsequent drying processes. This also applies to cases in which the dried active-substance layer is not removed again from parts of the surface.

According to an alternative embodiment, the electrode tip is porous at least in one partial area, the active substance being absorbed into the porous material. The recesses from which the active substance is released can in this case have structural sizes in the micrometer range. The porous volume area of the electrode tip is preferably connected to a reservoir inside the pacemaker electrode, from which, in particular by means of capillary forces, active substance is guided to the surface of the electrode tip.

In a particularly preferable embodiment, the electrode tip has through-openings from which the active substance is released. The through-openings, in contrast to openings in a porous body, have a defined geometric form and are preferably connected to an active-substance reservoir located inside the electrode tip or adjacent to the electrode tip. The openings which are fashioned as through-openings can be sealed at the surface of the electrode tip, as described above, with a material that clears the opening as a function of the temperature.

The avoidance of tissue fibrosis by means of continuous drug release from the electrode tip permits a particularly small design for the electrode tip. The surface area of the electrode tip is preferably less than 5 $mm^2$. Despite this small surface area, the stimulation threshold exhibits no time-dependency or only very slight time-dependency.

Pacemaker electrodes frequently have fixing elements for attaching the electrode head to the myocardium, as known in principle for example from DE 33 00 050 C2. In this case, bands or threads are provided as fixing elements which, on implantation of the pacemaker electrode, lie close to the surface thereof. The particular section of the electrode cable of the pacemaker to which the bands or threads are attached at their ends, can be compressed somewhat with the aid of a mandrin that runs through the electrode cable. This compression makes the bands or threads stand out from the pacemaker electrode in an arc shape and they are thus intended to develop their effect as fixing elements. A renewed displacement of the mandrin in the opposite direction is designed if required to stretch the bands or threads again, so that a change in position of the electrode tip is possible.

A further pacemaker electrode known from German patent DE 28 43 096 A1 has a fixing element which, in contrast to the fixing elements known from German patent DE 33 00 050 C2, has free ends which can penetrate into the tissue of the heart. Activation and deactivation of the fixing element are also designed to be possible in this case, a mandrin which is displaceable in the electrode cable likewise being provided for this purpose. To deactivate the fixing element, i.e. to fold in the free ends of the fixing element, a hook-shaped part of the mandrin is to be hooked into an eye-shaped part of the fixing element. However, this procedure might be difficult to execute with an implantable pacemaker electrode.

In order effectively to counter the disadvantages indicated above of conventional pacemaker electrodes, which are typically not intended for de-implantation, a preferred development of the invention provides for actuating a fixing element at the electrode tip by means of magnetic force. Here the fixing element suitable for attaching the electrode tip to the heart has an inherently variable geometry and/or is movably arranged relative to the electrode tip. An actuation element provided for moving the fixing element is in the simplest case a ferrous part which can be influenced by a magnetic field. Preferably, however, a magnet, in particular an electromagnet is provided as an actuation element. This magnet can be influenced by an external magnetic field, as is principally known for example from U.S. Pat. No. 6,241,671 B1, U.S. Pat. No. 6,330,467 B1 or DE 102 03 372 A1. Especially advantageous is the option of also being able to vary a magnetic field generated by an electromagnet in the pacemaker electrode when a pacemaker electrode is implanted, as is principally known for example from DE 102 03 371 A1.

The actuation element provided for reversible activation and deactivation of the fixing element is preferably arranged inside this actuation element, can however also be arranged in any way at another location in the pacemaker electrode and coupled mechanically to the fixing element. The fixing element preferably has at least one free end which can penetrate into the myocardium in the manner of a folding anchor.

In a preferred embodiment, an inherently at least approximately rigid fixing element is supported swivelably relative to the electrode tip on said electrode tip or on a part mechanically connected thereto. The pacemaker electrode preferably has at least two fixing elements which are arranged symmetrically in relation to an axis of symmetry running along the pacemaker electrode through the electrode tip.

The at least one fixing element is preferably supported sprung on the electrode tip or on a part mechanically connected thereto. The sprung support can in this case be fashioned such that the fixing element is in the folded-out or extended, i.e. active, position, as long as no magnetic force is being exerted on the fixing element. In this case, the fixing element must be moved during implantation of the pacemaker electrode by a force generated with the aid of an external magnetic field into the passive, i.e. folded-in or withdrawn position. The external magnetic field is thus needed during the entire implantation process, until such time as the electrode tip has reached its intended position at the heart.

Alternatively, it is also possible to support the fixing element in a bistable sprung manner, so that it is held without an external magnetic field both in the active position and in the passive position by means of sprung force. This variant of the sprung support of the fixing element has the advantage that the external magnetic field is needed only at the time of activation or deactivation of the fixing element.

According to an advantageous development, a plurality of actuation elements, in particular magnets, are provided for actuation of a particular fixing element and are arranged in particular within the fixing element. The individual actuation elements of the fixing element can in this case be fashioned so as to be of the same kind or different.

In this as also in all other embodiments, combinations of ferrous parts, permanent magnets and electromagnets can also be provided as actuation elements. The plurality of actuation elements per fixing element has the advantage that the individual actuation elements can be assigned different functions. For example, one actuation element can serve merely to fold out the fixing element and another actuation element merely to fold it in. Likewise, a first actuation element can be provided for blocking a specific positioning of the fixing element or for canceling the blocking, while a second actuation element changes the fixing element from the active to the passive state or vice versa.

Where the at least one actuation element needs a power supply, this runs through the electrode cable of the pacemaker electrode. A simultaneous transmission of stimulation pulses to the electrode tip and actuation of the fixing element or fixing elements is not required. For this reason, it is possible to use the same line to supply power to the actuation element as is also used for transmission of the stimulation pulses to the electrode tip. A suitable switching element can optionally be arranged in the electrode tip or in a section of the electrode cable adjoining the electrode tip.

With the aid of an external magnetic field, it is preferably possible, as also in other embodiments of the pacemaker electrode, to navigate the electrode tip overall in the body of the patient. A part within the pacemaker electrode enabling the controlled movement of the pacemaker electrode can in this case be identical to a component of the actuation element of the fixing element or to the actuation element overall.

A particularly advantageous option for further improving the suitability of the pacemaker for operation in magnetic fields lies in coating the electrode cable and/or the heart-pacemaker cable with a material which counteracts magnetic effects on the coated components. Especially suitable for this purpose are coatings of nanostructured materials, i.e. materials whose structural sizes, in particular particle sizes, are less than 100 nm.

The magnetic shielding of lines through nanostructured materials is principally known for example from the documents U.S. Pat. No. 6,506,972 B1, U.S. Pat. No. 6,713,671 B1 and U.S. Pat. No. 6,673,999 B1. Metal filaments for electromagnetic shieldings are known for example from U.S. Pat. No. 5,827,997 A. A method for the manufacture of substance mixtures with grain sizes of less than 100 nm is described in U.S. Pat. No. 5,540,959 A.

The pacemaker preferably has a low-pass filter for suppressing high-frequency magnetic fields. A low-pass filter in conjunction with a pacemaker, which is designed to be safe in relation to effects by magnetic resonance devices is described for example in U.S. Pat. No. 5,217,010 A.

In order to render the presence of the implanted pacemaker and associated data, including patient data, easily recognizable, the pacemaker in a preferred embodiment has an identification module, in particular in the form of an implantable RFID (radio frequency identification) chip. An associated RFID scanner, with the aid of which a pacemaker patient can be identified, can be set up for example in the entrance area of a clinic or of an examination room.

The advantage of the invention is in particular that, with the aid of an electrode cable which can be interrupted by at least one switching element and/or with the aid of a current-limiting element, pacemaker patients who are not for medical reasons compulsorily dependent on a permanent operation of the implanted pacemaker can use diagnosis and therapy facilities, in particular magnetic resonance devices, which were previously available only to patients without a pacemaker.

BRIEF DESCRIPTION OF THE DRAWINGS

Several exemplary embodiments of the invention are explained in detail below with reference to a drawing, in which in an outline simplified representation in each case.

Parts or parameters corresponding to one another are labeled with the same reference characters in all the figures.

DETAILED DESCRIPTION OF THE INVENTION

Figure 1:
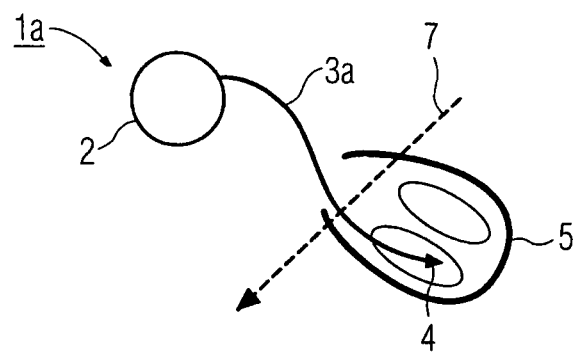
FIG. 1 shows a unipolar pacemaker according to the prior art.
Figure 2:
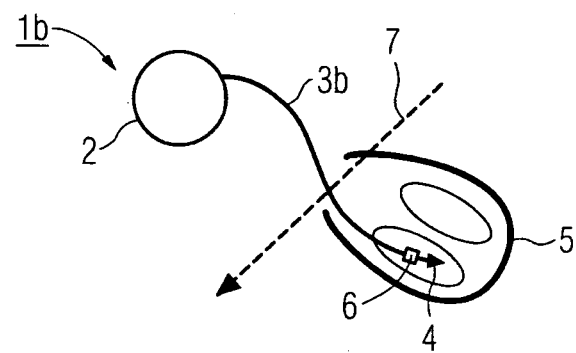
FIG. 2 shows a bipolar pacemaker according to the prior art.

FIGS. 1 and 2 show in greatly simplified form a unipolar pacemaker 1a and a bipolar pacemaker 1b, which respectively have a pacemaker housing 2 and a unipolar pacemaker electrode 3a or a bipolar pacemaker electrode 3b. The pacemaker electrode 3a, 3b is attached by means of an electrode tip 4 in the ventricle of a heart 5 and is provided for the transmission of stimulation pulses. As an alternative to the embodiments shown, a plurality of pacemaker electrodes 3a, 3b which are guided to the atrium and to the ventricle can be provided.

In the bipolar system (FIG. 2), an anode ring 6 is located about 2.5 cm away from the electrode tip 4. The function of the anode is assumed in the unipolar system (FIG. 1) by the pacemaker housing 2. In both systems, an external magnetic field 7 is indicated by a dashed arrow. If this magnetic field increases to values that are too high, then an electric current, which presents a serious risk for the patient, can be induced in the pacemaker electrode 3a, 3b. For this reason, patients with pacemaker systems according to FIGS. 1 and 2 are not examined with magnetic resonance devices.

Figure 3:
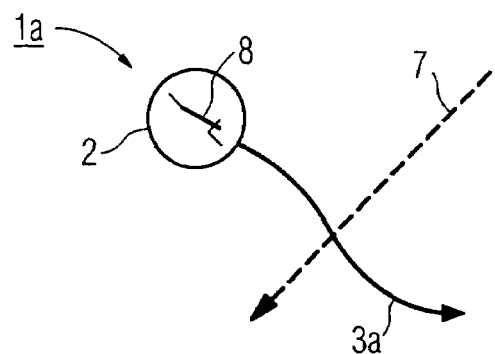
FIG. 3 shows a unipolar pacemaker according to the invention.
Figure 4:
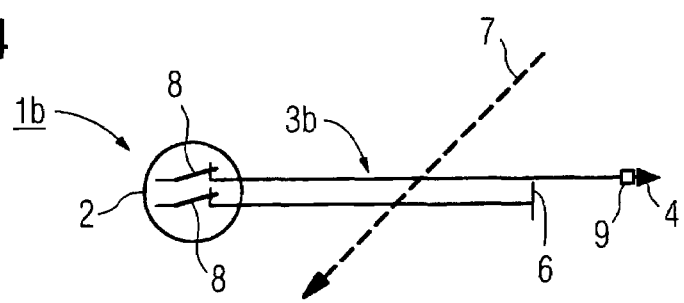
FIG. 4 shows a bipolar pacemaker according to the invention.

FIGS. 3 and 4 show in symbolic representation respectively a pacemaker 1a, 1b according to the invention in unipolar (FIG. 3) or bipolar (FIG. 4) embodiment. Here, the unipolar pacemaker electrode 3a according to FIG. 3 is equipped with a switch 8, the bipolar pacemaker electrode 3b according to FIG. 4 with two switches 8, generally also referred to as switching elements. The switches 8 open as soon as the magnetic field 7 exceeds a preferably adjustable threshold value and thus protect the patient against dangerous loadings through induced currents. In the exemplary embodiment according to FIG. 4, an electromagnet 9 which, in interaction with an external magnetic field, allows the pacemaker electrode 3b to be navigated in the body of the patient is located in the region of the electrode tip. Such magnetic navigation is also realizable in the exemplary embodiment according to FIG. 3. In both exemplary embodiments, a permanent magnet can also be used in place of the electromagnet 9.

Figure 5:
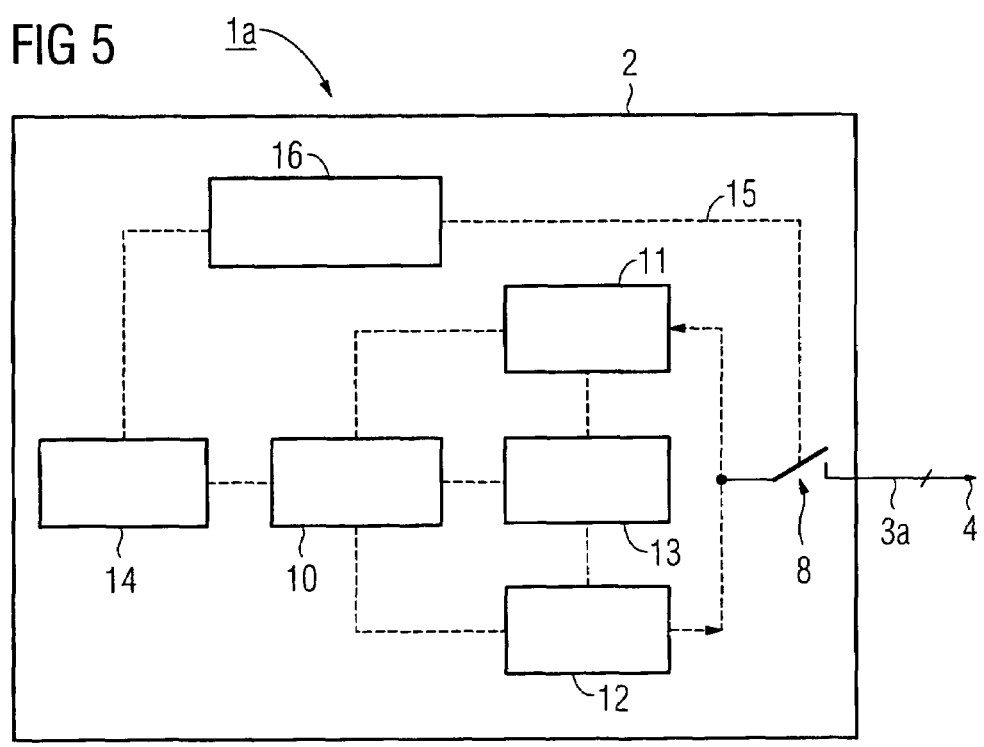
FIG. 5 shows a block diagram of the pacemaker according to FIG. 3.

FIG. 5 shows schematically the structure of the pacemaker 1a according to FIG. 3. Located in the pacemaker housing 2 is a monitoring and control unit 10 which interacts with a detection unit 11, which serves in detecting (sensing) signals outgoing from the heart 5, and with a pulse generator 12, which generates the pulses to be transmitted to the pacemaker electrode 3a. A battery 13 is provided for supplying power to the entire pacemaker 1a.

The pacemaker housing 2 also comprises a telemetry unit 14, which allows interrogation of the status of the pacemaker 1a and in particular enables switching of the switching element 8 from outside the patient. The switching element 8 is connected via a switching line 15 to a control unit 16. This control unit can have, in a manner not shown, an active connection to a current-monitoring unit. The components inside the pacemaker housing 2 shown in FIG. 5 are also located in an analogous manner in the pacemaker 1b of the exemplary embodiment according to FIG. 4.

Figure 6:
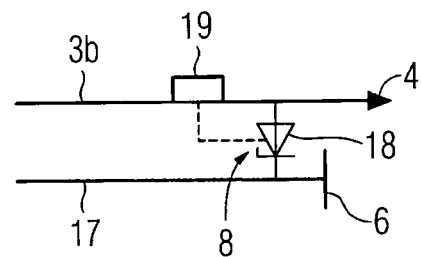
FIG. 6 shows a switching element of the pacemaker according to FIG. 4, featuring a Zener diode.
Figure 7:
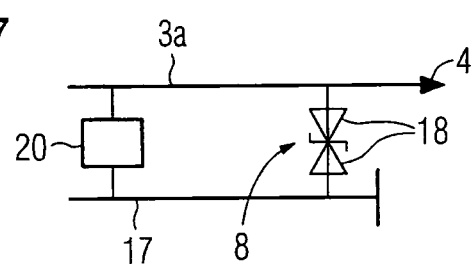
FIG. 7 shows a switching element of the pacemaker according to FIG. 4, featuring two Zener diodes.

FIGS. 6 and 7 show in detail exemplary embodiments of the switching element 8 serving to protect against effects of a magnetic field, which switching element limits the voltage between the conductor leading to the electrode tip 4 of the pacemaker electrode 3a, 3b and an anode cable 17. The switching element 8 comprises one or two Zener diodes 18, connected back to back, which form a limiter that produces a conductive connection when a specified induction voltage is exceeded.

The switching element in the embodiments according to FIG. 6 and FIG. 7 is suitable both for unipolar and for bipolar pacemaker systems. In the latter case, the switching element 8 can be arranged outside the pacemaker housing, in particular close to the anode ring 6. In a unipolar pacemaker system, the anode cable 17 is connected to the pacemaker housing 2.

Independently of the design of the pacemaker system, the at least one switching element 8 can also be realized as a complex integrated circuit, in particular in transistor or thyristor technology. FIG. 7 additionally shows symbolically a low-pass filter 20 which counteracts effects caused by high-frequency magnetic fields, as occur in particular in magnetic resonance examinations, and can be integrated into the switching element 8.

Figure 8:
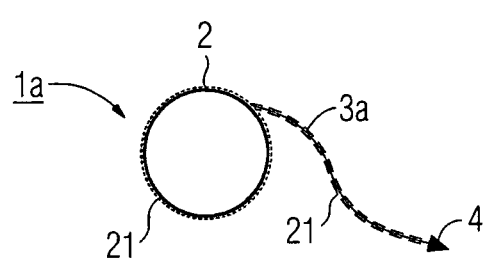
FIG. 8 shows a pacemaker with a coating of nanostructured material.

FIG. 8 shows a pacemaker 1a, the housing 2 and the electrode 3a of which have a coating 21 of a nanostructured material (particle size below 100 nm). The coating 21 is fashioned as a thin-film layer with particles of silicon dioxide, aluminum dioxide, silicon nitrate and/or carbon and reduces the current flow as well as the heat generation resulting from this in the protected components 2, 3a. In comparison with conventional screens in the form of films or other homogeneous materials in other areas of technology, the nanostructured coating 21 has in particular the advantage that reflections are reduced.

Figure 9:
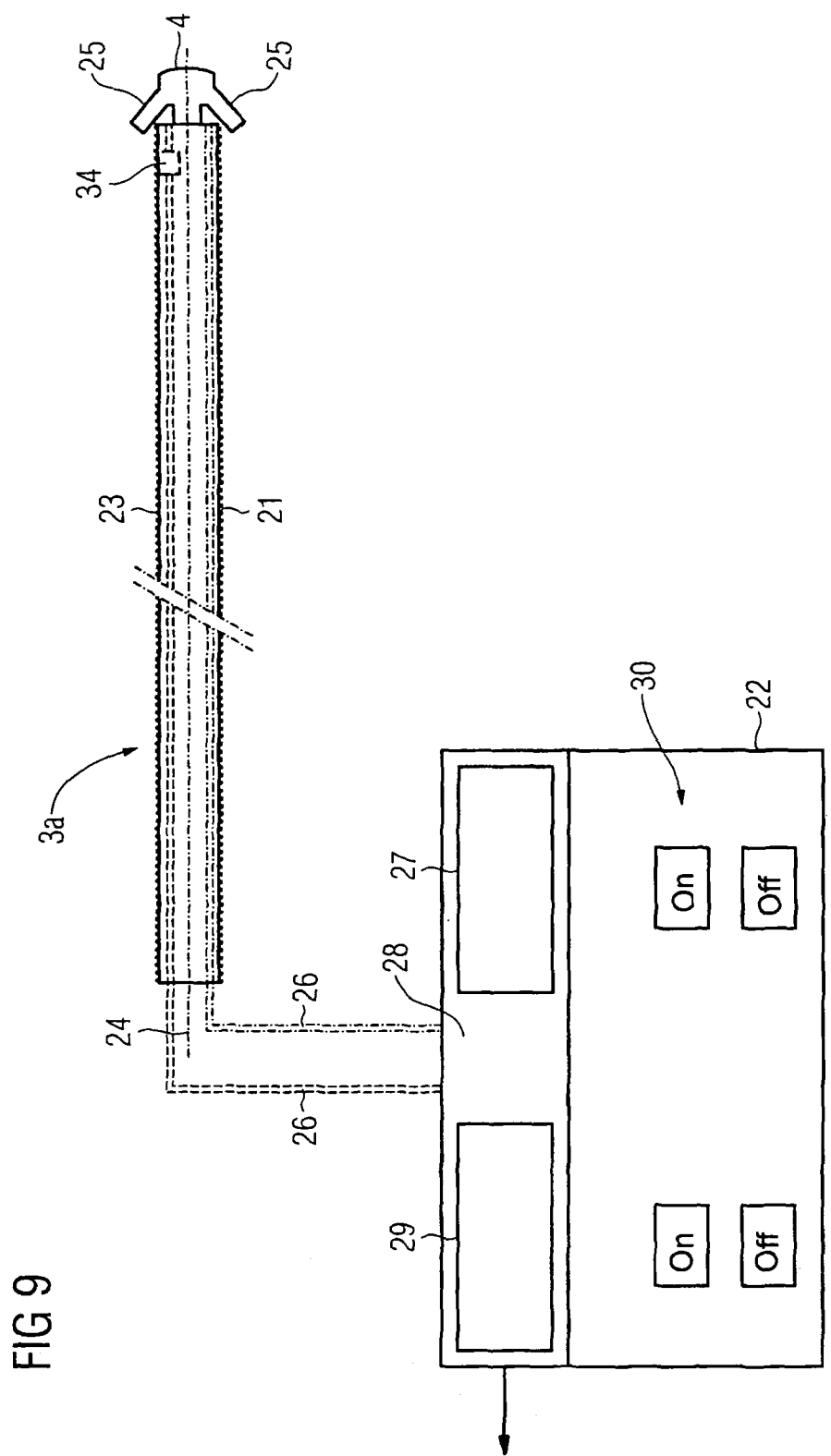
FIG. 9 shows a pacemaker electrode with a nanostructured coating, comprising magnetically actuatable fixing elements and a control unit, FIG. 10, 11 show a pacemaker electrode comprising an electrode tip suitable for release of an active substance, FIG. 12, 13 show a pacemaker electrode comprising an OCT measurement element and a signal-interface/drive unit.

FIG. 9 shows a pacemaker electrode 3a with a connected control device 22 which can be used on implantation of the pacemaker electrode 3a. An insulating sleeve 23 of the pacemaker electrode 3a is connected liquid-tight to the electrode tip 4 which functions as a cathode and to which a line 24 for the transmission of stimulation pulses to the heart leads. The pacemaker electrode 3a shown in FIG. 9 is part of a unipolar pacemaker system in which the pacemaker housing 2 (not shown here) serves as an anode. Equally, however, the system could also be fashioned as a bipolar system in which a separate anode is spaced about 2 to 3 cm from the electrode tip 4.

A stable, low-resistance coupling of the electrode tip 4 to the myocardium is of great importance in both unipolar and bipolar systems, particularly in the case of sensing via the pacemaker electrode 3a. Fixing elements 25, which are articulated at the electrode tip 4 and can be adjusted via connecting leads 26 from the control device 22, contribute substantively to this.

The control device 22 has, in addition to a power supply 27 and a control electronics 28, a connection module 29 which is provided for communication with a magnetic navigation system. The individual fixing elements 25 can be actuated separately in the exemplary embodiment according to FIG. 9 by means of operator buttons 30. Deviating from this exemplary embodiment, it is also possible always to actuate the fixing elements 25 simultaneously and/or to use the lead 24 for actuating the fixing elements 25.

An identification module 34 in the form of an RFID (radio frequency identification) chip is located inside the pacemaker electrode 3a close to the electrode tip 4. Deviating from the diagram, the RFID chip 34, which has the particular advantage that it can be read out without its own power supply, can also be implanted at another location as part of the pacemaker system.

Figure 10:
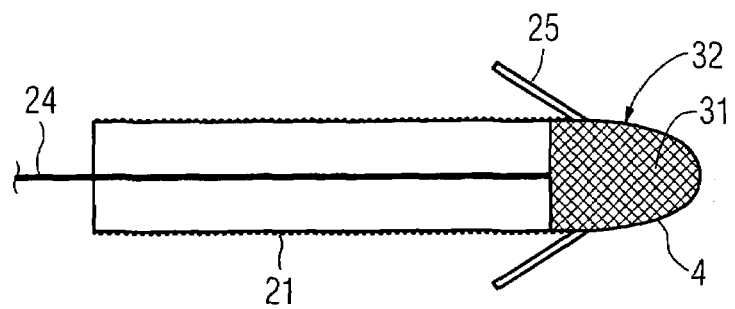
Figure 11:
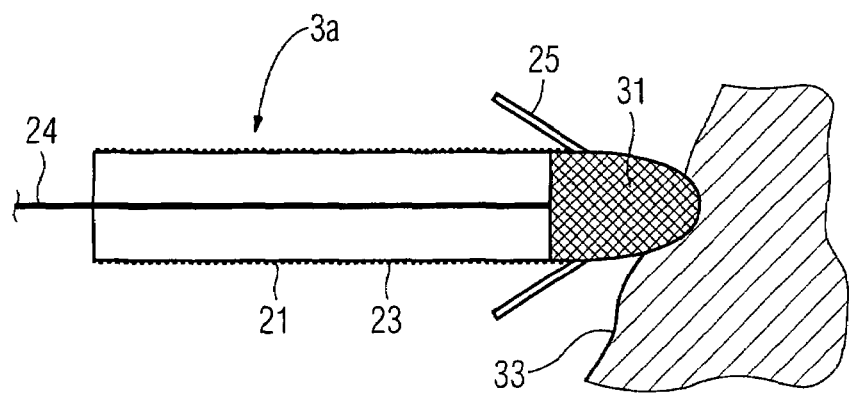

In the exemplary embodiment according to FIGS. 10 and 11, the electrode tip 4 is provided for releasing a drug. For this purpose, the surface labeled 31 of the electrode tip 4 is roughened such that discrete recesses 32 are formed. In FIGS. 10 and 11, these recesses are symbolized by a regular pattern, but may actually be stochastically distributed on the surface 31, even in microscopic form. A supply of a drug that is or contains one of the active substances sirolimus, paclitaxel, everolimus, fibrin, rapamycin and/or FK 506 is located in each recess 32. Furthermore, the electrode tip 4 is produced from a conductive material such as carbon, titanium or platinum. In particular, iridium, ceramic materials, aluminum dioxide, polymers or polyurethane can also be used as materials for forming in particular layers of the electrode tip 4. If necessary, an active substance can be applied in the form of a layer or in any other form not only to the electrode tip 4 but also to the insulating sleeve 23.

The active substance deposited in the recesses 32 for preventing tissue fibrosis at the contact point between the electrode tip 4 and the heart tissue is mixed on the one hand with an electrolyte that increases the conductivity and on the other with a substance that increases the surface adhesion. Together with the geometric design of the recesses 32 and the given chemical conditions in the body, this results in a drug release period in the implanted state of the pacemaker electrode 3a, as shown in FIG. 11, of about 3 months. Tissue fibrosis in the area of contact between the myocardium labeled 33 and the pacemaker electrode 3a is thereby permanently avoided.

Figure 14:
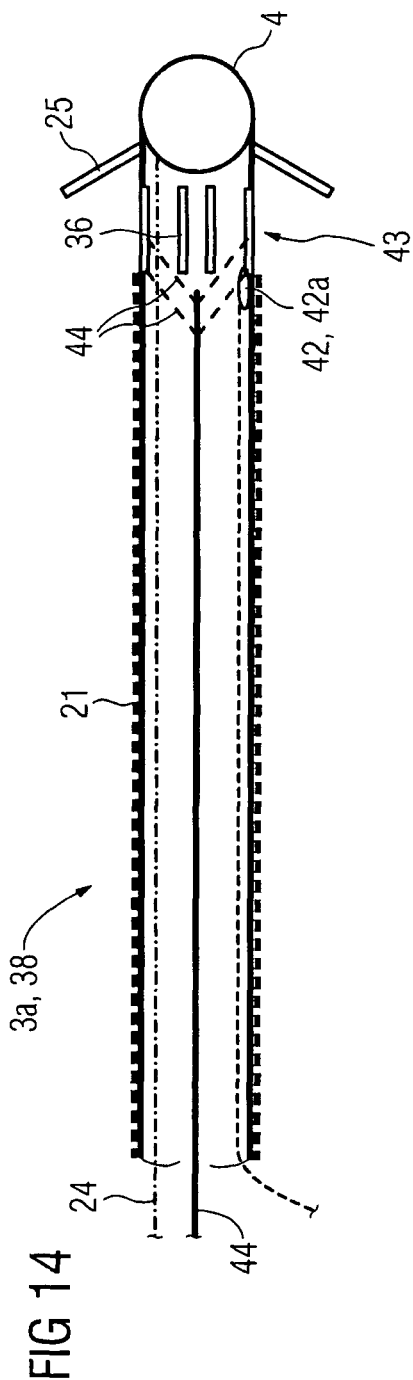
FIG. 14 shows a pacemaker electrode comprising an IVUS measurement element.

FIGS. 12 to 14 show embodiments of pacemaker systems with integrated measuring devices for imaging diagnoses. In particular, in the exemplary embodiment according to FIGS. 12 and 13, a measurement element 35 for optical coherence tomography (OCT) is shown and in the exemplary embodiment according to FIG. 14 a measurement element 36 for an ultrasound examination (IVUS) part of the pacemaker system.

In the exemplary embodiment according to FIGS. 12 and 13, the pacemaker electrode 3a accommodates an ultrasound catheter 37, referred to as an IVUS catheter for short. Similarly, the exemplary embodiment according to FIG. 14 provides an OCT catheter 38 which can also be configured as an integrated component with the pacemaker electrode 3a. The catheter 37 or 38 can, where it is provided for insertion into a sheath, be connected to a signal-interface/drive unit 41 for the IVUS or OCT examination with the aid of a mechanical linking system 40 comprising a rotation coupling 39. The OCT sensor 35 can be rotated about its own axis during the examination with the aid of the signal-interface/drive unit 41. The equivalent is in principle also possible with the IVUS sensor 36, but is not necessary in the exemplary embodiment according to FIG. 14, as the measurement element 36 provided for the ultrasound examination covers all angular ranges about the longitudinal axis of the pacemaker electrode 3a. In this case, an annular ultrasound sensor array 43 is located in the area of the pacemaker electrode 3a bordering the electrode head 4. Multiple control and signal lines 44 lead to the sensor array 23. The number of control and signal lines 44 guided through the pacemaker electrode 3a can be reduced (in a manner not shown in further detail) by using a multiplexer arranged on the ultrasound sensor array 43. In addition, the line 24 connected to the electrode head 4, said line serving the transmission of electrical pulses, can be used at least temporarily for the intravascular ultrasound measurement.

Independent of the type of measurement element 35, 36, a duct suitable for transferring a liquid, in particular a contrast means or a cooking salt solution, runs through the pacemaker electrode 3a, with an outlet opening 42 in the insulating sleeve 23. The liquid flowing through the pacemaker electrode 3a to the outlet opening 42 is indicated by a dashed line. The outlet opening 42 is fashioned as a miniaturized non-return valve 42a such that it allows the selective outflow of contrast means or cooking salt solution directly into the heart chamber, but prevents the ingress of blood into the lumen of the pacemaker electrode 3a. Thus, the measurement element 35, 36 does not come into contact with body fluid of the patient even in cases in which during the examination a liquid is guided through the pacemaker electrode 3a, and can be used repeatedly without sterilization. The non-return valve 42a is preferably manufactured using nanotechnology methods, i.e. in particular with methods used in the field of semiconductor technology including etching techniques and lithography. The same applies to other miniaturized parts of the intravenous pacemaker electrode 3a.

Figure 15:
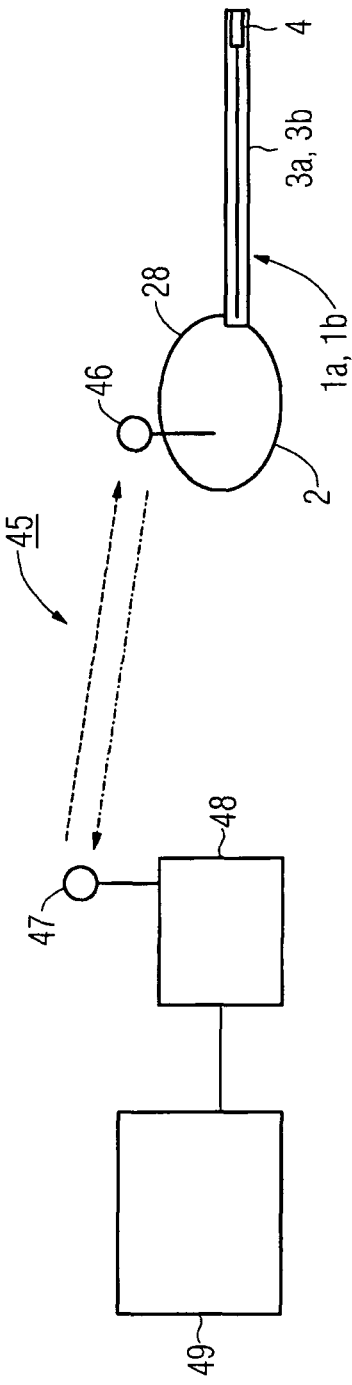
FIG. 15 shows a pacemaker comprising an IVUS measurement element, integrated in a telemetry system.

FIG. 15 shows integration of a pacemaker 1a, 1b according to one of the exemplary embodiments explained above into a telemetry system 45. In this case, the pacemaker 1a, 1b has a first transceiver unit 46 for wireless signals, in particular radio signals, arranged in the pacemaker housing 2 or connected thereto. A pre-processing and control unit (not shown in further detail) is also located within the pacemaker housing 2, said pre-processing and control unit being provided for a first processing of the data recorded by means of the pacemaker electrode 3a, 3b, in particular by sensing and/or by the measurement element 35, 36.

A second transceiver unit 47, also referred to as telemetry interface, communicates outside the body of the patient with the first transceiver unit 46, also referred to as telemetry module, which is thus located in the body of the patient. The telemetry interface 47 is in turn connected in a conducted or wireless manner to an evaluation unit 48. In this way, an examination, in particular an ultrasound examination, which can be externally influenced and evaluated, can be carried out not only during the implantation of the pacemaker electrode 3a, 3b, but also at any later point in time. In particular, a long-term monitoring of a patient is also possible by means of repeated examinations with the implanted pacemaker 1a, 1b. It is particularly advantageous to integrate a pacemaker electrode 3a according to FIG. 14 in the telemetry system 45 according to FIG. 15, since in this case no mechanical rotation of parts inside the pacemaker electrode 3a is necessary.

Functions of the evaluation unit 48 can also be realized wholly or in part inside the pacemaker 1a, 1b. Such a function is, for example, the computational consideration of the geometry of conducting parts, in particular cables, inside the pacemaker electrode 3a, 3b during an imaging examination, in particular IVUS or OCT examination. For this purpose, a data acquisition device 49, for example in the form of a scanner, is connected to the evaluation unit 48. The geometric and other relevant data of possible pacemaker electrodes 3a, 3b used is stored in a database and can be assigned to a barcode which is applied to the packaging of the pacemaker electrode 3a, 3b and is read with the aid of a data acquisition device 32. The evaluation unit 48 uses this data in order to optimize the measurement, for example by means of the measurement element 35, 36 and in particular to remove artifacts.

The invention claimed is:
1. A pacemaker used by a patient, comprising:
an implantable pacemaker housing;
a pulse generator arranged in the pacemaker housing that generates a stimulation pulse;
a pacemaker electrode that transmits the stimulation pulse to a heart of the patient;
a switching element that regulates a current flowing through the pacemaker electrode to the heart of the patient, the current being induced by an external magnetic field;
a telemetry unit that switches the switching element; and
an identification unit arranged inside the pacemaker electrode,
wherein the identification unit is a radio frequency identification chip,
wherein a stimulation threshold of the pacemaker is not affected by the external magnetic field when the pacemaker is active if the external magnetic field does not exceed an admissible threshold value,
wherein the pacemaker comprises a magnetically actuatable fixing element for fixing the pacemaker electrode,
wherein the switching element is reversibly actuatable for renewed activation of the pacemaker after a preceding shutdown, wherein the stimulation threshold of the pacemaker changes over time as a result of tissue fibrosis in a tip of the pacemaker electrode that may lead the pacemaker to no longer function, wherein the tip of the pacemaker electrode comprises a plurality of recesses for holding an active substance, and wherein the tissue fibrosis is prevented by a long-lasting release of the active substance from the tip of the pacemaker electrode so that the stimulation threshold of the pacemaker is not increased significantly.

2. The pacemaker as claimed in claim 1, wherein the switching element interrupts, reduces, or limits the current flowing through the pacemaker electrode.

3. The pacemaker as claimed in claim 1, wherein the external magnetic field is generated by a medical instrument during a medical examination of the patient.

4. The pacemaker as claimed in claim 1,
wherein the switching element is a semiconductor switching element, and
wherein the semiconductor switching element is integrated in a circuit.

5. The pacemaker as claimed in claim 1, wherein the switching element comprises a Zener diode or two Zener diodes connected back to back.

6. The pacemaker as claimed in claim 1, wherein the switching element is switched depending on a strength of the external magnetic field.

7. The pacemaker as claimed in claim 1, wherein the switching element comprises a non-ferromagnetic metal component.

8. The pacemaker as claimed in claim 1,
further comprising a magnet arranged on the pacemaker electrode for navigating the pacemaker electrode in the external magnetic field, and
wherein the magnet is an electromagnet or a permanent magnet.

9. The pacemaker as claimed in claim 1,
wherein a part of the pacemaker is coated with a material to counteract a magnetic effect of the external magnetic field,
wherein the coated part of the pacemaker is the pacemaker housing or the pacemaker electrode, and
wherein the material comprises a nanostructured material.

10. The pacemaker as claimed in claim 1, further comprising a low-pass filter arranged between an anode and a cathode of the pacemaker electrode.

11. The pacemaker as claimed in claim 1, wherein the pacemaker electrode comprises an ultrasound measurement element or an optical coherence tomography measurement element.

12. The pacemaker as claimed in claim 1, wherein the switching element is switched depending on a temperature of the pacemaker electrode.

13. The pacemaker as claimed in claim 1, wherein the recesses are sealed wells arranged on a surface of the tip of the pacemaker electrode.

14. The pacemaker as claimed in claim 1, wherein the recesses are sealed with a material that can be degraded as a function of temperature.

15. A method for protecting a patient carrying a pacemaker in a medical examination, comprising:
connecting a switching element to a pacemaker electrode;
operating the switching element to regulate a current flowing through the pacemaker electrode to a heart of the patient, the current being induced by an external magnetic field generated by a medical instrument during the medical examination;
switching the switching element via a telemetry unit; and
arranging an identification unit inside the pacemaker electrode,
wherein the identification unit is a radio frequency identification chip,
wherein a stimulation threshold of the pacemaker is not affected by the external magnetic field when the pacemaker is active if the external magnetic field does not exceed an admissible threshold value,
wherein the pacemaker comprises a magnetically actuatable fixing element for fixing the pacemaker electrode,
wherein the switching element is reversibly actuatable for renewed activation of the pacemaker after a preceding shutdown,
wherein the stimulation threshold of the pacemaker changes over time as a result of tissue fibrosis in a tip of the pacemaker electrode that may lead the pacemaker to no longer function,
wherein the tip of the pacemaker electrode comprises a plurality of recesses for holding an active substance, and
wherein the tissue fibrosis is prevented by a long-lasting release of the active substance from the tip of the pacemaker electrode so that the stimulation threshold of the pacemaker is not increased significantly.

16. The method as claimed in the claim 15, wherein the switching element interrupts, reduces, or limits the current flowing through the pacemaker electrode.

* * * * *